(12) United States Patent
Faig et al.

(10) Patent No.: US 12,109,293 B2
(45) Date of Patent: Oct. 8, 2024

(54) COSMETIC COMPOSITIONS WITH HIGH AMOUNTS OF LACTONE POLYOLS

(71) Applicant: L'OREAL, Paris (FR)

(72) Inventors: Jonathan James Faig, Sayreville, NJ (US); Yon Jae Yoon, Roselle, NJ (US); Rukil Patel, Parlin, NJ (US)

(73) Assignee: L'OREAL, Paris (FR)

( * ) Notice: Subject to any disclaimer, the term of this patent is extended or adjusted under 35 U.S.C. 154(b) by 1 day.

(21) Appl. No.: 18/148,707

(22) Filed: Dec. 30, 2022

(65) Prior Publication Data

US 2024/0216247 A1 Jul. 4, 2024

(51) Int. Cl.
*A61K 8/49* (2006.01)
*A61K 8/67* (2006.01)
*A61K 8/81* (2006.01)
*A61Q 19/08* (2006.01)

(52) U.S. Cl.
CPC .............. *A61K 8/498* (2013.01); *A61K 8/676* (2013.01); *A61K 8/8152* (2013.01); *A61Q 19/08* (2013.01)

(58) Field of Classification Search
CPC ...... A61K 8/498; A61K 8/676; A61K 8/8152; A61Q 19/08
See application file for complete search history.

(56) References Cited

U.S. PATENT DOCUMENTS

| 7,592,002 B2 | 9/2009 | Gupta |
| 9,931,288 B2 | 4/2018 | Philippon et al. |
| 11,389,390 B2 | 7/2022 | Arora et al. |
| 11,446,233 B2 | 9/2022 | Brieva et al. |
| 2009/0068255 A1* | 3/2009 | Yu .......................... A61P 35/00 424/59 |
| 2009/0169502 A1 | 7/2009 | Quadir |
| 2011/0268682 A1 | 11/2011 | Cannell et al. |
| 2021/0059907 A1 | 3/2021 | Samain et al. |
| 2021/0059908 A1 | 3/2021 | Samain |
| 2022/0047543 A1 | 2/2022 | Zhuk et al. |
| 2022/0096360 A1 | 3/2022 | Brieva et al. |
| 2022/0192961 A1 | 6/2022 | Stebbins et al. |
| 2022/0202671 A1 | 6/2022 | Stebbins et al. |
| 2022/0202691 A1 | 6/2022 | Saini et al. |
| 2022/0211599 A1 | 7/2022 | Stebbins et al. |
| 2022/0249342 A1 | 8/2022 | Mitra et al. |

FOREIGN PATENT DOCUMENTS

| KR | 1020220030095 | * | 3/2022 | ............... A61K 8/06 |
| WO | 9943296 A2 | | 9/1999 | |
| WO | 2017071820 A1 | | 5/2017 | |
| WO | 2022136902 A1 | | 6/2022 | |

OTHER PUBLICATIONS

Preliminary Search Report and Written Opinion issued on Oct. 12, 2023 for corresponding French Application No. FR 2302601.

* cited by examiner

*Primary Examiner* — Benjamin J Packard
*Assistant Examiner* — Joshua A Atkinson
(74) *Attorney, Agent, or Firm* — POLSINELLI PC

(57) ABSTRACT

The instant disclosure relates to a cosmetic composition containing high amounts of lactone polyols and to methods for treating skin with the compositions. The cosmetic compositions include: (a) poly C10-30 alkyl acrylate; (b) at least 5 wt. % of one or more lactone polyols; (c) one or more nonionic emulsifiers; (d) one or more fatty compounds; and (e) water. In addition, the amount of the one or more lactone polyols in the composition is typically at least 10-fold higher than the amount of the poly C10-30 alkyl acrylate in the composition.

20 Claims, No Drawings

COSMETIC COMPOSITIONS WITH HIGH AMOUNTS OF LACTONE POLYOLS

FIELD OF THE DISCLOSURE

The instant disclosure relates to cosmetic compositions that include high amounts of lactone polyols; and to methods for treating skin with the cosmetic composition.

BACKGROUND

Common problems associated with formulating cosmetic compositions comprising multiple components is compatibility of the components, stability, and aesthetic appeal. Many ingredients that are beneficial to the skin have unique physical and chemical characteristics limiting the amount that can be incorporated into cosmetic compositions. High amounts will jeopardize the integrity of the compositions and change the characteristics of the products. In addition, stability problems can cause partial, if not complete, loss of product integrity, color changes, malodor, viscosity changes, etc. Even if high amounts of certain ingredients can be incorporated into a cosmetic products, the resulting product may no longer have an appropriate texture, aesthetic look and feel, or functionality.

Many active ingredients are unstable and sensitive to temperature, pH, light, and oxidation. Therefore, encapsulation processes have been employed to protect them from unwanted degradation and used for controlling release of the active ingredient. Antioxidants, for example, are substances that protect ingredients such as fragrances, natural fats, and oils from unstable molecules known as free radicals. Antioxidants interact with and stabilize free radicals and prevent damage caused by free radicals. Typically, antioxidants should be soluble in the ingredients that are protecting. Butylated hydroxytoluene (BHT), butylated hydroxyanisole (BHA), and tocopherols (Vitamin E) are common oil soluble antioxidants. Propyl gallate is an example of a water-soluble antioxidant.

Many ingredients in cosmetics, especially anti-aging and skin care products are unstable and break down quickly when exposed to atmospheric oxygen, light, or heat. To counter such break down, active ingredients have been incorporated into complexes for protection, e.g., complexed with cyclodextrin. For example, retinol is a useful anti-wrinkle ingredient that is sensitive to oxygen and light. Complexing retinol with cyclodextrin has been found to provide a stabilizing effect to the retinol.

High pressure homogenizers can be used in the processing of compositions, including cosmetic compositions, to form products such as emulsions, creams, sunscreens, makeups, and fragrances. Homogenization is widely used in the cosmetics industry to produce homogenous and stable emulsions. Through high pressure homogenization, particle sizes can be reduced to help avoid phrase separation, distribute various ingredients homogenously, and to modify viscosity.

Many cosmetic compositions for treating skin aim to provide active ingredients for absorption into the skin. Skin acts as a natural barrier between internal and external environments and therefore plays an important role in vital biological functions such as protection against mechanical and chemical injury, microorganisms, and ultraviolet damage. The health and appearance of skin, however, can deteriorate due to environmental factors, genetic makeup, nutrition, and sun exposure.

Environmental pollution conditions are fast worsening and becoming more apparent in the daily life of consumers worldwide. The damage of pollution against human skin is also becoming more and more evident. Human skin is also subjected to a variety of insults by extrinsic factors such as ultraviolet (UV) radiation, environmental pollution, wind, heat, infrared radiation, low humidity, harsh surfactants, abrasives, etc. Recent studies suggest that in addition to UV radiation, other environmental factors contribute to the development of solar lentigines, particularly air pollution. Ultimately, these factors result in visible signs of skin damage including small brown patches on the skin, especially in the elderly.

Typical skin damage includes fine lines, wrinkling, hyperpigmentation, sallowness, sagging, dark under-eye circles, puffy eyes, enlarged pores, visible dead skin, i.e., flaking, scaling, dryness, and roughness. Consumers desire to slow the gaining of skin damage and reduce the effects of aging, especially in the face and around the eyes. Radiant and clear skin appears youthful and is a sign of good health and vitality. Accordingly, there is an ongoing need for new and improved formulations that improve the health and visual appearance of skin.

There is a need for compositions that deliver high amounts of skin active ingredients that aesthetically appealing, have pleasant tactile properties, and are easy to use. The inventors of the instant disclosure discovered unique cosmetic compositions and method of using the compositions that address these and other needs.

SUMMARY

The instant disclosure relates to cosmetic compositions that contain and deliver high amounts of lactone polyols to the skin. The compositions are stable, have pleasant tactile properties, are aesthetically appealing, and easy to use. Lactone polyols, for example, gluconolactone and/or 3-O-ethyl ascorbic acid, tend to cause compositions to be tacky (sticky), especially when used in high amounts. The inventors discovered that poly C10-30 alky acrylate surprisingly eliminates or greatly reduces the tackiness caused by lactone polyols, for example, gluconolactone and/or 3-O-ethyl ascorbic acid, even when lactone polyols is used in high amounts.

The cosmetic compositions provide exceptional cosmetic properties to the skin, due in part to the high amount of lactone polyols. The high amounts of lactone polyols in the compositions dissolve dead skin cells, improve the appearance of fine lines and discoloration, and helps remove and minimize excess from the skin. The cosmetic composition also improve skin texture and tone, hydrate the skin, and offer antioxidant benefits. The cosmetic composition include:
 (a) poly C10-30 alkyl acrylate;
 (b) at least 5 wt. % of lactone polyols, based on the total weight of the cosmetic composition;
  wherein the lactone polyols of (b) is in an amount at least 10-fold higher than an amount of the poly C10-30 alkyl acrylate of (a);
 (c) one or more nonionic emulsifiers;
 (d) one or more fatty compounds; and
 (e) water.

In some cases, the composition is in the form of an oil-in-water emulsion or an oil-in-water dispersion.

Nonlimiting examples of nonionic emulsifiers include fatty acid esters of sucrose, fatty acid esters of polyethylene glycol, glyceryl esters of fatty acids, alkanolamides, ethoxylate amides, alkylated alcohols, alkylpolypolyglucosides, sorbitan esters, polyol esters and ethoxylates, ethylene glycol ethers of fatty alcohols, fatty alcohol ethoxylates, and a mixture thereof.

Non-limiting examples of fatty compounds include oils, mineral oil, alkanes (paraffins), fatty alcohols, fatty acids, fatty alcohol derivatives, fatty acid derivatives, esters of fatty alcohols, hydroxy-substituted fatty acids, waxes, fatty esters, fatty carbonate esters, triglyceride compounds, lanolin, silicone oils, and mixtures thereof.

The viscosity of the composition can optionally be adjusted and enhanced by including one or more thickening agents. Nonlimiting examples of thickening agents include taurate polymers and copolymers, carboxylic acid polymers, crosslinked polyacrylate polymers, polyacrylamide polymers, polysaccharides, gums, modified gums, and a combination thereof. In various embodiments, at least one of the one more thickening agents is a taurate polymer or copolymer and/or a polyacrylates crosspolymer.

In various embodiments, the cosmetic compositions include one or more alpha hydroxy acids, beta hydroxy acids, or a combination. In further embodiments, the cosmetic composition includes at least one alpha hydroxy and at least one beta hydroxy acid. The cosmetic compositions may include a plurality of alpha hydroxy acids and/or beta hydroxy acids. For example, the compositions may include one or more lactone polyols, one or more alpha hydroxy acids (e.g., glycolic acid, lactic acid, etc.), and one or more beta hydroxy acids (e.g., salicyclic acid).

Nonlimiting examples of alpha hydroxy acids include glycolic acid, lactic acid, phytic acid, citric acid, malic acid, tartaric acid, a salt thereof, and a combination thereof. Nonlimiting examples of beta hydroxy acids include salicylic acid, beta-hydroxybutanoic acid, tropic acid, trethocanic acid, and a combination thereof.

Non-limiting examples of useful fatty compounds include oils, waxes, alkanes (paraffins), fatty alcohols, fatty acids, fatty esters, fatty carbonate esters, triglyceride compounds, lanolin, hydrocarbons, derivatives thereof, and mixtures thereof.

In various embodiments, at least one of the one or more fatty compounds is a fatty alcohol. Fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cis4-t-butylcyclohexanol, myricyl alcohol and a mixture thereof. In some cases, the fatty alcohols are selected from myristyl alcohol, cetyl alcohol, stearyl alcohol, isostearyl alcohol, oleyl alcohol, isotridecyl alcohol, and a mixture thereof. In some cases, the fatty alcohols are selected from solid fatty alcohols, for example, solid fatty alcohols selected from cetyl alcohol, stearyl alcohol, behenyl alcohol and mixtures thereof, preferably cetyl alcohol, behenyl alcohol, cetearyl alcohol, and a combination thereof.

In various embodiments, at least one of the one or more fatty compounds is a fatty ester or a fatty carbonate ester.

In various embodiments, at least one of the one or more fatty compounds is a volatile hydrocarbon. Nonlimiting examples of volatile hydrocarbons include isoparaffin, isohexadecane, isododecane, isodecane, undecane, tridecane, dodecane, isohexyl, isodecyl, neopentanoate, C15-19 alkane, and a combination thereof.

In various embodiments, the cosmetic compositions include one or more water-soluble solvents include, for example, glycerin, alcohols (for example, $C_{1-30}$, $C_{1-15}$, $C_{1-10}$, or $C_{1-4}$ alcohols), polyols (polyhydric alcohols), glycols (e.g., butylene glycol, caprylyl glycol, etc.), and a mixture thereof.

Another aspect of the instant disclosure relates to methods for treating skin. The methods include applying the cosmetic composition according to the instant disclosure to the skin, in particular the skin of the face. For example, the methods dissolve dead skin cells, improve the appearance of fine lines and discoloration, remove excess oil from the skin, improve skin texture and tone, hydrates the skin, and offers antioxidant benefits to the skin.

DETAILED DESCRIPTION

With aging, the outer skin layer (epidermis) thins, even though the number of cell layers remains unchanged. The number of pigment-containing cells (melanocytes), however, decreases. Therefore, the skin appears pale and translucent. Large, pigmented spots (age spots, liver spots, or lentigos) may appear in sun-exposed areas. Changes in the connective tissue reduce the skin's strength and elasticity. This is known as elastosis. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively influence the skin, causing dryness, rash, and puffiness.

Human skin acts as a primary barrier between the body and its environment. Crucial for this skin barrier function is the lipid matrix in the outermost layer of the skin (epidermis), the stratum corneum (SC). Two of its functions are (1) to prevent excessive water loss through the epidermis and (2) to avoid that compounds from the environment permeate into the viable epidermal and dermal layers and thereby provoke an immune response. The composition of the SC lipid matrix is dominated by three lipid classes: cholesterol, free fatty acids, and ceramides. These lipids adopt a highly ordered, 3-dimensional structure of stacked densely packed lipid layers (lipid lamellae): the lateral and lamellar lipid organization. The way in which these lipids are ordered depends on the composition of the lipids. One very common skin disease in which the SC lipid barrier is affected is atopic dermatitis (AD).

The cosmetic compositions of the instant case are particularly useful for treating skin, especially the skin of the face. The cosmetic composition may be in the form of an oil-in-water emulsion or dispersion. The cosmetic compositions typically include:
  (a) poly C10-30 alkyl acrylate;
  (b) at least 5 wt. % of lactone polyols;
      wherein the lactone polyols of (b) is in an amount at least 10-fold higher than an amount of the poly C10-30 alkyl acrylate of (a);
  (c) one or more nonionic emulsifiers;
  (d) one or more fatty compounds;
  (e) water;
  (f) optionally, one or more thickening agents;
  (g) optionally, one or more alpha hydroxy acids, beta hydroxy acids, salts thereof, or a combination thereof
  (h) optionally, one or more water-soluble organic solvents
  (i) optionally, one or more miscellaneous ingredients;
      wherein all weight percentages are based on a total weight of the composition.

Poly C10-30 alkyl acrylate is a polymer of the ester of acrylic acid and C10-30 alcohol. The inventors discovered that inclusion of poly C10-30 alkyl acrylates in the cosmetic compositions is particularly effective at reducing the tackiness of the compositions caused, at least in part, to the inclusion of lactone polyols. Use of poly C10-30 alkyl acrylates allows for higher amounts of lactone polyols to be used in the compositions while retaining an acceptable tackiness (stickiness). The total amount of the poly C10-30 alkyl acrylates in the compositions will vary. Nonetheless, in various embodiments, the total amount of the poly C10-30 alkyl acrylates in the cosmetic compositions is from about 0.1 to about 5 wt. %, based on the total weight of the cosmetic composition. In further embodiments, the total amount of the poly C10-30 alkyl acrylates in the cosmetic compositions is from about 0.1 to about 3 wt. %, about 0.1 to about 2 wt. %, about 0.1 to about 1 wt. %, about 0.2 to about 5 wt. %, about 0.2 to about 3 wt. %, about 0.2 to about 2 wt. %, about 0.2 to about 1 wt. %, about 0.3 to about 5 wt. %, about 0.3 to about 3 wt. %, about 0.3 to about 2 wt. %, about 0.3 to about 1 wt. %, about 0.5 to about 5 wt. %, about 0.5 to about 3 wt. %, about 0.5 to about 2 wt. %, or about 0.5 to about 1 wt. %, based on the total weight of the cosmetic composition.

Gluconolactone and 3-O-ethyl ascorbic acid are useful for improving the health and look of the skin. For example, they lift dead skins cells from the skin surface, increase skin thickness, decrease wrinkles, help hydrate the skin, etc. The compositions of the instant disclosure are unique in that they include high amounts of lactone polyols, for example, at least 1 or 2 wt. %, based on the total weight of the cosmetic composition. In various embodiments, the total amount of the one or more lactone polyols in the cosmetic compositions is at least 1 to about 20 wt. %, at least 1 to about 15 wt. %, at least 1 to about 10 wt. %, at least 1 to about 8 wt. %, at least 2 to about 20 wt. %, at least 2 to about 15 wt. %, at least 2 to about 10 wt. %, about 2 to about 8 wt. %, at least 3 to about 20 wt. %, at least 3 to about 15 wt. %, at least 3 to about 10 wt. %, at least 3 to about 8 wt. %, at least 5 to about 20 wt. %, at least 5 to about 15 wt. %, at least 5 to about 12 wt. %, at least 5 to about 10 wt. %, at least 5 to about 8 wt. %, based on the total weight of the cosmetic composition.

The total amount of lactone polyol in the cosmetic compositions of the instant disclosure exceeds the total amount poly C10-30 alkyl acrylate. The total amount of lactone polyol exceeds the total amount poly C10-30 alkyl acrylate. For example, in various embodiments, the total amount of the one or more lactone polyols is at least 10-form higher than the total amount of the poly C10-30 alkyl acrylate. For example, the total amount of the one or more lactone polyols may be at least 10-fold to about 25-fold higher, at least 10-fold to about 20-fold higher, at least 10-fold to about 18-fold higher, at least 10-fold to about 15-fold higher, or at 10-fold to about 12-fold higher than the total amount of poly C10-30 alkyl acrylate. Stated another way, the weight ratio of the gluconolactone to the poly C10-30 alkyl acrylate is at least 10:1 to about 25:1, at least 10:1 to about 25:1, at least 10:1 to about 20:1, at least 10:1 to about 18:1, about 10:1 to about 15:1, or about 10:1 to about 12:1 (lactone polyols:poly C10-30 alkyl acrylate).

Nonlimiting examples of nonionic emulsifiers include fatty acid esters of sucrose, fatty acid esters of polyethylene glycol, glyceryl esters of fatty acids, alkanolamides, ethoxylate amides, alkylated alcohols, alkylpolypolyglucosides, sorbitan esters, polyol esters and ethoxylates, ethylene glycol ethers of fatty alcohols, fatty alcohol ethoxylates, and a mixture thereof. A more exhaustive but nonlimiting list of useful nonionic emulsifiers is provided below under the heading "Nonionic Emulsifiers."

The total amount of nonionic emulsifiers in the cosmetic compositions will vary. In various embodiments, the total amount of nonionic emulsifiers is from about 0.05 to about 6 wt. % of the total weight of the cosmetic composition. For example, the total weight of the nonionic emulsifiers may range from about 0.05 to about 6 wt. %, 0.05 to about 5 wt. %, 0.05 to about 4 wt. %, 0.05 to about 3 wt. %; from 0.1 to about 6 wt. %, 0.1 to about 5 wt. %, 0.1 to about 4 wt. %, 0.1 to about 3 wt. %; from 0.5 to about 6 wt. %, 0.5 to about 5 wt. %, 0.5 to about 4 wt. %, 0.5 to about 3 wt. %; from 0.8 to about 6 wt. %, 0.8 to about 5 wt. %, 0.8 to about 4 wt. %, 0.8 to about 3 wt. %; from 1 to about 6 wt. %, 1 to about 5 wt. %, 1 to about 4 wt. %, or 1 to about 3 wt. %, based on the total weight of the cosmetic composition.

Non-limiting examples of fatty compounds include oils, mineral oil, alkanes (paraffins), fatty alcohols, fatty acids, fatty alcohol derivatives, fatty acid derivatives, esters of fatty alcohols including fatty carbonate esters, hydroxy-substituted fatty acids, waxes, triglyceride compounds, lanolin, silicone oils, and mixtures thereof.

In various embodiments, at least one of the one or more fatty compounds is a fatty alcohol. Nonlimiting examples of fatty alcohols include fatty alcohols selected from C14-22 alcohols, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the cosmetic compositions preferably include cetyl alcohol, behenyl alcohol, cetearyl alcohol, and a mixture thereof. A more exhaustive but nonlimiting list of fatty compounds is provided below, under the heading "Fatty Compounds."

The total amount of the one or more fatty alcohols, if present, will vary. Nonetheless, in various embodiments, the total amount of the one or more fatty alcohols is about 0.1 to about 5 wt. %, based on the total weight of the cosmetic composition. In further embodiments, the total amount of the one or more fatty alcohols is from about 0.1 to about 4 wt. %, about 0.1 to about 3 wt. %, about 0.5 to about 5 wt. %, about 0.5 to about 4 wt. %, or about 0.5 to about 3 wt. %, based on the total weight of the cosmetic composition.

In various embodiments, at least one of the one or more fatty compounds is an ester of fatty alcohol, such as a fatty carbonate ester. Nonlimiting examples of fatty carbonate esters include dialkyl carbonates of formula: $R_1O(C=O)OR_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof. In additional cases, the fatty compound is a fatty ester chosen from cetyl ester, purcellin oil (cetearyl octanoate), isopropyl myristate, isopropyl palmitate, C12-C15 alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, diisostearyl malate, neopentyl glycol dioctanoate, dibutyl sebacate, di-C12-13 alkyl malate, dicetearyl dimer dilinoleate, dicetyl adipate, diisocetyl adipate, diisononyl adipate, diisostearyl dimer dilinoleate, diisostearyl fumarate, and a mixture thereof.

The total amount of the one or more ester of fatty alcohol, such as a fatty carbonate esters, if present, will vary. Nonetheless, in various embodiments, the total amount of the one or more ester of fatty alcohols is from about 0.1 to about 15 wt. %, about 0.1 to about 10 wt. %, about 0.1 to about 8 wt. %, about 0.5 to about 15 wt. %, about 0.5 to about 12 wt. %, about 0.5 to about 10 wt. %, about 0.5 to about 8 wt. %, about 1 to about 15 wt. %, about 1 to about 12 wt. %, about 1 to about 10 wt. %, about 1 to about 8 wt. %, about 2 to about 15 wt. %, about 2 to about 12 wt. %, about 2 to about 10 wt. %, or about 2 to about 8 wt. %, based on the total weight of the cosmetic composition.

In various embodiments, at least one of the one or more fatty compounds is a volatile hydrocarbon. Nonlimiting examples of volatile hydrocarbons include volatile hydrocarbon-based oils such as, for example, volatile hydrocarbons include volatile hydrocarbon-based oils such as, for example, volatile hydrocarbon oils having from 8 to 20 carbon atoms and their mixtures and in particular branched $C_8$ to $C_{20}$ alkanes such as $C_8$ to $C_{20}$ isoalkanes (also known as isoparaffins), isododecane, isodecane, isohexadecane, and for example, the oils sold under the trade names of Isopar or Permethyl, the $C_8$ to $C_{20}$ branched esters such as isohexyl or isodecyl neopentanoate, alcohols, and their mixtures. In certain embodiments, the cosmetic composition include Isohexadecane, C15-19 alkane, or a combination thereof.

The total amount of the one or more volatile hydrocarbons in the cosmetic composition, if present, will vary. Nonetheless, in various embodiments, the total amount of the one or more volatile hydrocarbons is from about 0.1 to about 15 wt. %, about 0.1 to about 10 wt. %, about 0.1 to about 8 wt. %, about 0.5 to about 15 wt. %, about 0.5 to about 12 wt. %, about 0.5 to about 10 wt. %, about 0.5 to about 8 wt. %, about 1 to about 15 wt. %, about 1 to about 12 wt. %, about 1 to about 10 wt. %, about 1 to about 8 wt. %, about 2 to about 15 wt. %, about 2 to about 12 wt. %, about 2 to about 10 wt. %, or about 2 to about 8 wt. %, based on the total weight of the cosmetic composition.

In various embodiments, the one or more fatty compounds are selected from fatty alcohols, esters of fatty alcohols including fatty carbonate esters, volatile hydrocarbons, and a combination thereof.

Nonlimiting examples of thickening agents include taurate polymers and copolymers, carboxylic acid polymers, crosslinked polyacrylate polymers, polyacrylamide polymers, polysaccharides, gums, modified gums, and a combination thereof. In various embodiments, at least one of the one more thickening agents is a taurate polymer or copolymer and/or a polyacrylates crosspolymer. In preferred embodiments, the cosmetic compositions include one or more thickening agents selected from taurate polymers and copolymers, crosslinked polyacrylate polymers, and a combination thereof. In additional preferred embodiments, at least one of the one or more thickening agents is a taurate polymer or copolymer.

Nonlimiting examples of taurate polymers and copolymers include acrylamide/sodium acryloyl dimethyl taurate copolymer, ammonium polyacryloyldimethyl taurate, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, or a mixture thereof, preferably hydroxyethyl acrylate/sodium acryloyldimethyl taurate copolymer, ammonium acryloyldimethyl taurate/VP copolymer, ammonium polyacryloyldimethyl taurate, or a mixture thereof.

The total amount of the one or more thickening agents will vary. Nonetheless, in various embodiments, the total amount of the one or more thickening agents is about 0.1 to about 8 wt. %, based on the total weight of the cosmetic composition. In further embodiments, the total amount of the one or more thickening agents is from about 0.1 to about 5 wt. %, about 0.1 to about 4 wt. %, about 0.1 to about 3 wt. %, about 0.1 to about 2 wt. %, about 0.5 to about 8 wt. %, about 0.5 to about 5 wt. %, about 0.5 to about 4 wt. %, about 0.5 to about 3 wt. %, or about 0.5 to about 2 wt. %, based on the total weight of the cosmetic composition.

The amount of water in the cosmetic compositions can and will vary depending on the amount of the other components in the cosmetic compositions. In an embodiment, the total amount of water in the compositions can range from about 50 to about 85 wt. %, based on the total weight of the cosmetic composition. In various embodiments, the amount of water in the cosmetic composition can range from about 50 to about 80 wt. %, about 50 to about 75 wt. %, about 50 to about 70 wt. %, about 55 to about 80 wt. %, about 55 to about 75 wt. %, about 55 to about 70 wt. %, about 60 to about 85 wt. %, about 60 to about 80 wt. %, about 60 to about 75 wt. %, about 60 to about 70 wt. %, based on the total weight of the cosmetic composition.

Alpha hydroxy acids and beta hydroxy acids are known in the art. In certain embodiments, the cosmetic compositions may include a plurality of one or more alpha hydroxy acids, beta hydroxy acids, optionally polyhydroxy acids, or a mixture thereof. In various embodiments, the compositions include one or more lactone polyols, one or more alpha hydroxy acids (e.g., glycolic acid, lactic acid, etc.), and one or more beta hydroxy acids (e.g., salicyclic acid). In further embodiments, the cosmetic composition may include one or more alpha hydroxy acids but no beta hydroxy acid or one or more beta hydroxy acids but no alpha hydroxy acids, in addition to the one or more lactone polyols.

Nonlimiting examples of alpha hydroxy acids include glycolic acid, lactic acid, phytic acid, citric acid, malic acid, tartaric acid, a salt thereof, and a combination thereof. Nonlimiting examples of beta hydroxy acids include salicylic acid, beta-hydroxybutanoic acid, tropic acid, trethocanic acid, and a combination thereof.

The total amount of the one or more alpha hydroxy acid, if present, will vary. Nonetheless, in various embodiments, the cosmetic compositions includes about 0.1 to about 10 wt. %, about 0.1 to about 8 wt. %, about 0.1 to about 6 wt. %, about 0.5 to about 10 wt. %, about 0.5 to about 8 wt. %, about 0.5 to about 6 wt. %, about 1 to about 10 wt. %, about 1 to about 8 wt. %, about 1 to about 6 wt. %, about 2 to about 10 wt. %, about 2 to about 8 wt. %, about 2 to about 6 wt. %, about 3 to about 10 wt. %, about 3 to about 8 wt. %, about 3 to about 6 wt. %, about 4 to about 10 wt. %, about 4 to about 8 wt. %, about 4 to about 6 wt. %, about 5 to about 10 wt. %, about 5 to about 8 wt. %, or about 5 to about 6 wt. %, based on the total weight of the cosmetic composition.

The total amount of the one or more beta hydroxy acids, if present, will vary. Nonetheless, in various embodiments, the total amount of the one or more beta hydroxy acids is from about 0.01 to about 5 wt. %, based on the total weight of the cosmetic composition. In further embodiments, the total amount of the one or more beta hydroxy acids is from about 0.01 to about 3 wt. %, about 0.01 to about 2 wt. %, about 0.01 to about 1 wt. %, about 0.1 to about 5 wt. %, about 0.1 to about 3 wt. %, about 0.1 to about 2 wt. %, about 0.1 to about 1 wt. %, based on the total weight of the cosmetic composition.

The cosmetic composition may include one or more miscellaneous ingredients. The cosmetic compositions of the instant disclosure may optionally include one or more miscellaneous ingredients. Miscellaneous ingredients are ingredients that are compatible with the cosmetic compositions and do not disrupt or materially affect the basic and novel properties of the cosmetic compositions. Miscellaneous ingredients commonly used in cosmetics are known in the art. Non-limiting examples include preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, colorants, mattifying agents, further skin active agents, depigmenting agents, anti-wrinkle agents, etc. A more exhaustive but nonlimiting list of miscellaneous ingredients is provided below, under the heading "Miscellaneous Ingredients."

Miscellaneous ingredients can be included in the cosmetic composition, for example, in an amount of about 0.01 to about 10 wt. %, based on the total weight of the cosmetic composition. The total amount of the one or more miscellaneous ingredients may be about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 1 to about 10 wt. %, about 1 to about 8 wt. %, about 1 to about 5 wt. %, or about 1 to about 3 wt. %, based on the total weight of the cosmetic composition.

In various embodiments, the cosmetic compositions include one or more water-soluble solvents include, for example, glycerin, alcohols (for example, $C_{1-30}$, $C_{1-15}$, $C_{1-10}$, or $C_{1-4}$ alcohols), polyols (polyhydric alcohols), glycols (e.g., butylene glycol, caprylyl glycol, etc.), and a mixture thereof. In some cases, the one or more water-soluble organic solvents are selected from glycerin, $C_2$-$C_5$ mono-alcohols, polyols (polyhydric alcohols), glycols, and a mixture thereof. A more exhaustive but nonlimiting list of water-soluble organic solvents is provided below, under the heading "Water-Soluble Organic Solvents."

The total amount of the one or more water-soluble solvents, if present, will vary. Nonetheless, in various embodiments, the total amount of the one or more water-soluble solvents is from about 0.01 to about 20 wt. %, based on the total weight of the cosmetic composition. In further embodiments, the total amount of the one or more water-soluble solvents is from about 0.01 to about 15 wt. %, about 0.01 to about 10 wt. %, about 0.01 to about 5 wt. %, about 0.1 to about 15 wt. %, about 0.1 to about 10 wt. %, about 0.1 to about 5 wt. %, about 0.1 to about 3 wt. %, about 1 to about 15 wt. %, about 1 to about 10 wt. %, about 1 to about 5 wt. %, about 3 to about 15 wt. %, or about 5 to about 10 wt. %, based on the total weight of the cosmetic composition.

Nonionic Emulsifiers

Examples of nonionic emulsifiers that may, in some cases, be suitably incorporated into the cosmetic composition include and/or may be chosen from alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mole of ethylene oxide; ethoxylated oils from plant origin; fatty acid esters of sucrose; fatty acid esters of polyethylene glycol; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

As glyceryl esters of fatty acids, glyceryl stearate (glyceryl mono-, di- and/or tristearate) (INCI name: glyceryl stearate) or glyceryl ricinoleate and mixtures thereof can be cited. As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Additionally or alternatively, the nonionic emulsifiers may comprise or be selected from alkanolamides, polyglucosides, sorbitan derivatives (not including the hydration of sorbitan to derive sorbitol), and polyol esters.

Alkanolamide(s)

Non-limiting examples of alkanolamides include fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides may include those formed by reacting an alkanolamine and a $C_6$-$C_{36}$ fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA, which is commercially available under the tradename EMPILAN from Innospec Active Chemicals.

Fatty acid alkanolamides include those of the following structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof); wherein $R_5$ is selected from —$CH_2OH$, —$CH_2CH_2OH$, —$CH_2CH_2CH_2OH$, —$CH_2(CHOH)_4CH_2OH$, -benzyl, and mixtures thereof; and wherein $R_6$ is selected from —H, —$CH_3$, —$CH_2OH$, —$CH_2CH_3$, —$CH_2CH_2OH$, —$CH_2CH_2CH_2OH$, —$CH_2(CHOH)_4CH_2OH$, -benzyl, and mixtures thereof.

In some instances, the one or more of the fatty acid alkanolamides include one or more acyl glucamides, e.g., acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide Alkyl Polyglucoside(s)

In some embodiments, the one or more alkyl polyglucosides include those chosen from lauryl glucoside, octyl glucoside, decyl glucoside, coco glucoside, caprylyl/capryl glucoside, sodium lauryl glucose carboxylate, and a mixture thereof. In some cases, the alkyl polyglucosides includes or is chosen from lauryl glucoside. Additionally or alternatively, the alkyl polyglucosides may be chosen from glycerol ($C_6$-$C_{24}$)alkylpolyglycosides including, e.g., polyethoxylated fatty acid mono or diesters of glycerol ($C_6$-$C_{24}$) alkylpolyglycosides. Additional alkyl polyglucosides that may be suitably incorporated, in some instances, in the cosmetic composition includes alkyl polyglucosides having a structure according to the following formula:

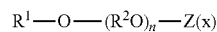

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Useful alkyl poly glucosides may, in some instances, include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

Sorbitan Derivative(s)

Suitable sorbitan derivatives that may be incorporated into the plurality of nonionic emulsifiers include those chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE (4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate and sorbitan tristearateand a mixture thereof.

Additional and/or alternative sorbitan derivatives include sorbitan esters including, e.g., esters of $C_{16}$-$C_{22}$ fatty acid and of sorbitan that were formed by esterification, with sorbitol, of at least one fatty acid comprising at least one saturated or unsaturated linear alkyl chain respectively having from 16 to 22 carbon atoms. These esters can be chosen in particular from sorbitan stearates, behenates, arachidates, palmitates or oleates, and their mixtures. Examples of optional sorbitan esters include sorbitan monostearate (INCI name: Sorbitan stearate) sold by Croda under the name Span 60, the sorbitan tristearate sold by Croda under the name Span 65 V, the sorbitan monopalmitate (INCI name: Sorbitan palmitate) sold by Croda under the name Span 40, the sorbitan monooleate sold by Croda under the name Span 80 V or the sorbitan trioleate sold by Uniqema under the name Span 85 V. A preferable sorbitan ester is sorbitan tristearate.

Polyol Ester(s)

Non-limiting examples of polyol esters include those chosen from alkoxylated polyol esters. For instance, the alkoxylated polyol esters may be chosen from pegylated derivatives of propylene glycol oleate, propylene glycol caprylate/caprate, propylene glycol cocoate, propylene glycol stearate, and a mixture thereof. In certain embodiments, the alkoxylated polyol esters are chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof. In some instances, the polyol ester is or includes PEG-55 propylene glycol oleate. Additionally and/or alternatively, the polyol esters may be chosen from ethoxylated fatty acid esters of sorbitan comprising from 2 to 30 mol of ethylene oxide.

In some cases, the polyol ester may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

Sources of unsaturated polyol esters of glycerol include synthesized oils, natural oils (e.g., vegetable oils, algae oils, bacterial derived oils, and animal fats), combinations of these, and the like. Non-limiting examples of vegetable oils include Abyssinian oil, Almond oil, Apricot oil, Apricot Kernel oil, Argan oil, Avocado oil, Babassu oil, Baobab oil, Black Cumin oil, Black Currant oil, Borage oil, Camelina oil, Carinata oil, Canola oil, Castor oil, Cherry Kernel oil, Coconut oil, Corn oil, Cottonseed oil, Echium oil, Evening Primrose oil, Flax Seed oil, Grape Seed oil, Grapefruit Seed oil, Hazelnut oil, Hemp Seed oil, Jatropha oil, Jojoba oil, Kukui Nut oil, Linseed oil, Macadamia Nut oil, Meadowfoam Seed oil, Moringa oil, Neem oil, Olive oil, Palm oil, Palm Kernel oil, Peach Kernel oil, Peanut oil, Pecan oil, Pennycress oil, Perilla Seed oil, Pistachio oil, Pomegranate Seed oil, Pongamia oil, Pumpkin Seed oil, Raspberry oil, Red Palm Olein, Rice Bran oil, Rosehip oil, Safflower oil, Seabuckthorn Fruit oil, Sesame Seed oil, Shea Olein, Sunflower oil, Soybean oil, Tonka Bean oil, Tung oil, Walnut oil, Wheat Germ oil, High Oleoyl Soybean oil, High Oleoyl Sunflower oil, High Oleoyl Safflower oil, High Erucic Acid Rapeseed oil, combinations of these, and the like. Non-limiting examples of animal fats include lard, tallow, chicken fat, yellow grease, fish oil, emu oil, combinations of these, and the like. Non-limiting example of a synthesized oil includes tall oil, which is a byproduct of wood pulp manufacture. In some embodiments, the natural oil is refined, bleached, and/or deodorized.

The polyol esters may optionally be a natural polyol esters chosen from vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, in one aspect, sucrose, and mixtures thereof.

Additional non-limiting examples of nonionic emulsifiers that may optionally be used in the cosmetic composition include and/or may be chosen from alkanolamides; polyoxyalkylenated nonionic emulsifiers; polyglycerolated nonionic emulsifiers; ethoxylated fatty esters; alcohols, alphadiols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated oils from plant origin; fatty acid esters of sucrose; fatty acid esters of polyethylene glycol; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Fatty Compounds

The term "fatty compounds" is interchangeable with the "fatty materials." Fatty compounds are known as compounds that are not soluble (or only sparingly soluble) in water; they are hydrophilic and are often solubilized in organic solvents. They include materials such as oils, fats, waxes, hydrocarbons, fatty esters, etc. For purposes of the instant disclosure, "fatty compounds." For purposes of the instant disclosure "silicone oils" are considered fatty compounds. Non-limiting examples of useful fatty compounds include oils, waxes, alkanes (paraffins), fatty acids, fatty esters, triglyceride compounds, lanolin, hydrocarbons, silicones, and derivatives thereof, and mixtures thereof. Fatty compounds are described by the International Federation Societies of Cosmetic Chemists, for example, in Cosmetic Raw Material Analysis and Quality, *Volume 1: Hydrocarbons, Glycerides, Waxes and Other Esters* (Redwood Books, 1994), which is incorporated herein by reference in its entirety.

Non-limiting examples of fatty compounds include oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, silicone oils, and mixtures thereof.

The cosmetic composition of the instant disclosure includes one or more fatty alcohols. The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the cosmetic compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

Non-limiting examples of useful fatty alcohols include lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol), and mixtures thereof.

In certain embodiments, the one or more fatty alcohols have from 12 to 24 carbon atoms. Specific nonlimiting examples include C14-22 alcohols, cetyl alcohol, stearyl alcohol, cetearyl alcohol, behenyl alcohol, lauryl alcohol, myristic or myristyl alcohol, arachidyl alcohol, lignoceryl alcohol, or mixtures thereof.

Preferably, the cosmetic composition includes one or more solid fatty alcohols, for example, chosen from C14-22 alcohols, cetyl alcohol, stearyl alcohol, behenyl alcohol and mixtures thereof, preferably cetyl alcohol, behenyl alcohol, cetearyl alcohol, and mixtures thereof.

The fatty alcohol(s) may be liquid or solid. However, in certain embodiments, it is preferable that the cosmetic compositions include at least one solid fatty alcohol, in particular saturated fatty alcohols that are solid at 25° C., preferably having at least 12 carbon atoms.

In some instances, the cosmetic compositions include one or more fatty alcohols selected from C14-22 alcohols, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the cosmetic compositions preferably include cetyl alcohol, behenyl alcohol, and cetearyl alcohol.

Fatty Acids

In some instances, the fatty compounds include fatty acids, fatty acid derivatives, esters of fatty acids, and hydroxyl-substituted fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Waxes

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

Non-Silicone Oils

In some instances, the fatty compounds may include or be chosen from one or more oil(s). Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the cosmetic compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Silicone Oils

Nonlimiting examples of silicone oils include dimethicone, dimethiconol, dimethiconol, cyclomethicone, polysilicone-11, phenyl trimethicone, trimethylsilylamodimethicone, and stearoxytrimethylsilane. In a preferred embodiment, the one or more silicones oils are non-volatile silicon oils. Useful silicone oils include polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates. Other examples of silicone oils that may be mentioned include volatile linear or cyclic silicones, such as those with a viscosity 8 centistokes (8×106 m2/s) and/or containing from 2 to 7 silicon atoms. These silicones optionally comprise alkyl or alkoxy groups containing from 1 to 10 carbon atoms. Non-limiting examples of volatile silicone oils include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, or mixtures thereof.

In a preferred embodiment, the cosmetic compositions include one or more silicone oils chosen from dimethicone, dimethiconol, cyclomethicone, polysilicone-11, phenyl trimethicone, and amodimethicone, preferably dimethicone.

In an embodiment, cosmetic compositions include one or more amino functionalized silicones. Nonlimiting examples include amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. Amodimethicone is a particularly useful amino functionalized silicone.

In a preferred embodiment the one or more silicone oils are chosen from dimethicone, dimethiconol, cyclopentasiloxane, cyclomethicone, cyclotetrasiloxane, cyclohexasiloxane, cycloheptasiloxane, decamethylcyclopentasiloxane, cyclotetrasiloxane, cyclotrisiloxane, capryldimethicone, caprylyl trimethicone, caprylyl methicone, cetearylmethicone, hexadecylmethicone, hexylmethicone, lauryl methicone, myristyl methicone, phenyl methicone, stearyl methicone, stearyl dimethicone, behenyl dimethicone, trifluoropropyl methicone, cetyl dimethicone, polyphenylmethylsiloxane, dimethylpolysiloxane, methylphenylpolysiloxane, methyltrimethicone, diphenylsiloxyphenyl trimethicone, and phenyl trimethicone, and mixtures thereof. Preferably, the one or more silicone oils include dimethicone, and optionally one or more further silicone oils.

In some embodiments, one or more fatty compounds may be selected from caprylic/capric triglyceride, cetyl alcohol, coco-caprylate-caprate squalene, a vegetal oil, behenyl alcohol, cetearyl alcohol, dicaprylyl carbonate, C15-19 alkane, isohexadecane, hydrogenated jojoba oil, or a mixture thereof.

In some embodiments, the cosmetic composition may include one or more fatty compounds chosen from fatty esters (such as isononyl isononanoate), polyolefins (such as petrolatum), waxes, squalane, squalene, hydrogenated polyisobutene, hydrogenated polydecene, polybutene, mineral oil, pentahydrosqualene, plant and/or vegetable oil, hydrocarbon-based oils (such as isohexadecane), silicone oils (such as dimethicone), or a mixture thereof.

The term "volatile hydrocarbon" is a hydrocarbon that is volatile at ambient temperature (25° C.) and normal pressure (1 atm). The term "volatile" as used herein with respect to a "volatile hydrocarbon" means any hydrocarbon capable of evaporating on contact with the skin or the lips in less than one hour at room temperature and atmospheric pressure. Examples of suitable volatile hydrocarbons include volatile hydrocarbon-based oils such as, for example, volatile hydrocarbon oils having from 8 to 20 carbon atoms and their mixtures and in particular branched $C_8$ to $C_{20}$ alkanes such as $C_8$ to $C_{20}$ isoalkanes (also known as isoparaffins), isododecane, isodecane, isohexadecane, and for example, the oils sold under the trade names of Isopar or Permethyl, the $C_8$ to $C_{20}$ branched esters such as isohexyl or isodecyl neopentanoate, alcohols, and their mixtures.

The volatile hydrocarbons may be in the form of an oil. The term "oil" is understood to mean a compound which is liquid at ambient temperature (25° C.) and normal pressure (1 atm), and which, when it is introduced in a proportion of at least 1% by weight into water at 25° C. is not soluble in water or soluble to a level of less than 10% by weight, with respect to the weight of oil introduced into the water. The term "hydrocarbon oil" is oil comprising hydrogen and carbon atoms, and containing no silicon atoms.

Thickening Agents

Non-limiting examples of thickening agents that may be included in the cosmetic compositions are set forth below.

I. Non-Mineral Thickening Agents

Non-mineral thickening agents, if present, may be lipophilic or hydrophilic, i.e., they may be appropriate for thickening an oily phase or an anhydrous composition or they may be appropriate for thickening an aqueous phase or an aqueous composition. For anhydrous compositions, lipophilic thickening agents or thickening agents that thicken anhydrous (e.g., oily) compositions are useful. Similarly, for aqueous compositions, hydrophilic thickening agents are useful.

Non-limiting examples of the non-mineral thickening agents useful for thickening anhydrous compositions include $C_{12-22}$ alkyl acrylate/hydroxyethylacrylate copolymer (INTELIMER), ethylene diamine/stearyl dimer dilinoleate copolymer such as OLEOCRAFT LP-10-PA-(MV) sold by Croda, polyamide-8 such as OLEOCRAFT LP-20-PA-(MV) sold by Croda, poly $C_{10}$-$C_{30}$ alkyl acrylate such as INTELIMER IPA 13-6 or INTELIMER IPA 13-1 NG Polymer sold by Air Products & Chemicals, nylon-611/dimethicone copolymer such as Dow Corning 2-8179 Gellant sold by Dow Corning, or dextrin palmitate such as RHEOPEARL KL2-OR sold by Chiba Flour Milling.

Additional non-limiting examples of non-mineral thickening agents useful for thickening anhydrous compositions include thickening polymers such as block copolymers of styrene with isoprene, butadiene, ethylene/propylene or ethylene/butylene including those presently available under the trade name KRATON, and particularly hydrogenated styrene/isoprene linear diblock copolymers. A related category of thickening polymer comprises polymers of alpha methylstyrene and styrene, such as those under the trade name KRISTALEX. Yet another thickening polymer comprises alkyl substituted galactomannan available under the trade name N-HANCE AG. Non-mineral thickening agents useful for thickening anhydrous compositions may also include thickening polymers such as vinyl pyrrolidone with polyethylene containing at least 25 methylene units, such as triacontanyl polyvinylpyrrolidone, under the trade name Antaron WP-660.

Non-limiting examples of non-mineral thickening agents may, optionally, be included for thickening aqueous compositions include xanthan gum, guar gum, biosaccharide gum, cellulose, acacia Seneca gum, sclerotium gum, agarose, pechtin, gellan gum, hyaluronic acid. Additionally, the one or more non-mineral thickening agents may be polymeric thickening agents such as, for example, ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer.

Additional, non-limiting examples of various types of non-mineral thickening agents include:

Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickening agents useful herein are those selected from carbomers, acrylates/C10-C30 alkyl acrylate crosspolymers, and mixtures thereof.

Crosslinked Polyacrylate Polymers

The compositions of the present disclosure can optionally contain crosslinked polyacrylate polymers useful as thickening agents or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™, provided by CS11 from Michel Mercier Products Inc.

Gums

Other thickening and gelling agents useful herein include materials which are primarily derived from natural sources. Non-limiting examples of these thickening and/or gelling agent include gums such as those chosen from acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic hetero-polysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

II. Mineral Thickening Agents

Mineral thickening agents are mineral based compounds that thicken or modify the viscosity of the skin tightening compositions. Non-limiting examples of mineral thickening agents include silica silylate, fumed silica, zeolite, natural clay, synthetic clay, kaolin, hectorite, organically modified hectorite (e.g., INCI: pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite), and a mixture thereof.

In some instances, the skin tightening compositions may include one or more mineral thickening agents selected from optionally modified silicas, optionally modified clays, and a mixture thereof. The mineral thickening agents may be selected from optionally modified silicas, optionally modified clays, and a mixture thereof. In some instance, the mineral thickening agents are chosen from lipophilic (organophilic) clays, in particular modified hectorites; hydrophobic-treated fumed silica; hydrophobic silica aerogels, and mixtures thereof (e.g., disteardimonium hectorite, silica silylate, or a mixture thereof).

The mineral thickening agents may be selected from silica silylate, fumed silica, zeolite, natural clay, synthetic clay, kaolin, hectorite, organically modified hectorite (e.g., INCI: 30 pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite).

Optionally Modified Silicas

Optionally modified silicas include fumed silica optionally subjected to a hydrophobic surface treatment, the particle size of which may be less than 1 μm. Specifically, it is possible to chemically modify the surface of the silica, by chemical reaction generating a reduced number of silanol groups present at the surface of the silica. Silanol groups can in particular be replaced by hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as "silica silylate" according to the CTFA (6th edition, 1995). They are sold, for example, under the references Aerosil R812 by the company Degussa, and Cab-O-Sil TS-53 by the company Cabot;

dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold, for example, under the references Aerosil R972 and Aerosil R974 by the company Degussa, and Cab-O-Sil TS-610 and Cab-O-Sil TS-720 by the company Cabot.

The hydrophobic fumed silica in particular may have a particle size that is nanometric to micrometric, for example ranging from about 5 to 200 nm.

The optionally modified silicas may, for instance, be silica aerogel particles. Silica aerogels are porous materials obtained by replacing (by drying) the liquid component of a silica gel with air. They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles may have a specific surface area per unit mass ($S_M$) ranging from 500 to 1500 $m^2/g$, preferably from 600 to 1200 $m^2/g$ and better still from 600 to 800 $m^2/g$, and a size expressed as the volume mean diameter (D[0.5]) ranging from 1 to 1500 μm, better still from 1 to 1000 μm, preferably from 1 to 100 μm, in particular from 1 to 30 μm, more preferably from 5 to 25 μm, better still from 5 to 20 μm, and even better still from 5 to 15 μm. In some instances, the hydrophobic silica aerogel particles have a size expressed as volume-mean diameter (D[0.5]) ranging from 1 to 30 μm, preferably from 5 to 25 μm, better still from 5 to 20 μm and even better still from 5 to 15 μm.

The hydrophobic silica aerogel particles may have a specific surface area per unit mass (SM) ranging from 600 to 800 m$^2$/g and a size expressed as the volume mean diameter (D[0.5]) ranging from 5 to 20 μm and even better still from 5 to 15 μm. The hydrophobic silica aerogel particles may have a specific surface area per unit of volume S$_V$ ranging from 5 to 60 m$^2$/cm$^3$, preferably from 10 to 50 m$^2$/cm$^3$ and better still from 15 to 40 m$^2$/cm$^3$.

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups. In some instances, it is particularly useful to use hydrophobic silica aerogel particles surface-modified with trimethylsilyl groups. Mention may be made of the aerogels sold by the company Cabot under the references Aerogel TLD 201, Aerogel OGD 201, Aerogel TLD 203, Enova Aerogel MT 1100 and Enova Aerogel MT 1200. Particularly useful aerogels include hydrophobic silica aerogels, preferably of silyl silica (INCI name: silica silylate).

Optionally Modified Clays

Clays are silicates containing a cation that may be chosen from calcium, magnesium, aluminum, sodium, potassium and lithium cations, and mixtures thereof. Examples of such material include, but are not limited to clays of the smectite family, and also of the vermiculite, stevensite and chlorite families. These clays can be of natural or synthetic origin.

Mention may particularly be made of smectites, such as saponites, hectorites, montmorillonites, bentonites or beidellite and in particular synthetic hectorites (also known as laponites), such as the products sold by Rockwood Additives Limited under the names Laponite XLS, Laponite XLG, Laponite RD, Laponite RDS and Laponite XL21 (these products are sodium magnesium silicates and in particular sodium lithium magnesium silicates); bentonites, such as the product sold under the name Bentone HC by Rheox; magnesium aluminum silicates, which are in particular hydrated, such as the products sold by Vanderbilt Company under the name Veegum Ultra, Veegum HS or Veegum DGT, or also calcium silicates and in particular that in synthetic form sold by the company under the name Micro-Cel C.

In some instances, organophilic clays are preferred, more particularly modified clays, such as montmorillonite, bentonite, hectorite, attapulgite and sepiolite, and mixtures thereof. The clay may be optionally modified bentonite or an optionally modified hectorite. Clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made of hectorites modified with a quaternary amine, more specifically with a C$_{10}$ to C$_{22}$ fatty acid ammonium halide, such as a chloride, such as hectorite modified with distearyldimethylammonium chloride (CTFA name: Disteardimonium hectorite), for instance the product sold under the name Bentone 38V, Bentone 38V CG or Bentone EW CE by the company Elementis, or stearalkonium hectorites, such as Bentone 27 V. In some instances, the clay is preferably disteardimonium hectorite.

Mention may also be made of quaternium-18 bentonites, such as those sold under the names Bentone 34 by the company Elementis, Tixogel VP by the company United Catalyst and Claytone 40 by the company Southern Clay; stearalkonium bentonites, such as those sold under the names Tixogel LG by the company United Catalyst and Claytone AF and Claytone APA by the company Southern Clay; or quaternium-18/benzalkonium bentonites, such as that sold under the name Claytone HT by the company Southern Clay. In some instances, it is preferable that the clay is chosen from organophilic modified clays, in particular organophilic modified hectorites, in particular modified with distearyldimethylammonium chloride (CTFA name: Disteardimonium hectorite).

Water-Soluble Organic Solvents

In various embodiments, the cosmetic compositions of the instant disclosure optionally include one or more water-soluble organic solvents. The term "water-soluble organic solvent" is interchangeable with the term "water-miscible organic solvent" and means a compound that is liquid at 25° C. and at atmospheric pressure (760 mmHg), and it has a solubility of at least 50% in water under these conditions. In an embodiment, the water-soluble organic solvents have a solubility of at least 60%, 70%, 80%, or 90%. Nonlimiting examples of water-soluble solvents include glycerin, monoalcohols, polyols (polyhydric alcohols), glycols, and a mixture thereof. In an embodiment, the one or more water-soluble solvents may be chosen from glycerin, propylene glycol, butylene glycol, pentylene glycol, dipropylene glycol, ethanol, isopropanol, t-butyl alcohol, and a mixture thereof.

Additional non-limiting examples include monoalcohols and polyols such as ethyl alcohol, isopropyl alcohol, propyl alcohol, isopropyl alcohol, benzyl alcohol, 4-tert-butylcyclohexanol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble organic solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2- imidazolidinone, formamide, acetamide, dimethyl sulfoxide, sorbit, sorbitan, acetine, diacetine, triacetine, sulfolane, and a mixture thereof.

Polyhydric alcohols are also useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In a preferred embodiment, the cosmetic compositions of the instant disclosure include one or more glycols selected from glycerin, propylene glycol, butylene glycol, pentylene glycol, dipropylene glycol, and mixtures thereof.

Miscellaneous Ingredients

Nonlimiting examples of various miscellaneous ingredients that may optionally be include (or excluded) from the cosmetic compositions is provided below.

Antioxidants

Examples of antioxidants include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ-tocotrienol, d-delta-tocotrienol) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, emblica officinalis, and bioflavonoids from rose hip and citrus may be used including water soluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E, and other carotenoids.

Flavonoids can also function as antioxidants. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcumin, bis-Desmethoxycurcumin, Tetrahydrocurcumin, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (*Sesamum indicum*) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

Skin Active Agents

Nonlimiting examples of skin active agents include madecassoside, retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate; —derivatives particularly copper and copper pidolate as *Cuivridone Solabia*—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of *Terminalia chebula*, nasturtium and of bioavailable zinc (microalgae), such as that sold under the name Seborilys Green Tech; —extracts of *Pygeum afrianum* such as that sold under the name *Pygeum afrianum* sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed laminaria extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by sociétéLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of cinchona bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

Depigmenting Agents

Nonlimiting examples of depigmenting agents include alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, certain compounds derived from plants such as chamomile, bearberry, the aloe family (*vera, ferox, bardensis*), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

Anti-Wrinkle Agent

The term "anti-wrinkle agent" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Nonlimiting examples of anti-wrinkle agents include: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinoids other than retinol (as discussed above, such as retinol palmitate), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular laminaria, bacterial extracts, the sapogenins such as diosgenin and extracts of *Dioscorea* plants, in particular wild yam, comprising: the a-hydroxy acids, b-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof. In at least one case, the skin tightening composition includes adenosine derivatives, such as non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

As already noted, skin active agents may be included as one or more of the miscellaneous ingredients. With respect to the total amount of skin active agents in the cosmetic compositions, if present, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; about 0.1 to about 10 wt. %, about 0.1 to about 5 wt. %, about 0.1 to about 2.5 wt. %, about 0.1 to about 1 wt. %, about 0.1 to about 0.5 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, or about 4 to about 6 wt. %, based on the total weight of the cosmetic composition.

pH

The pH of the cosmetic composition can vary but is typically less than 7, i.e., it is acidic. In various embodiments, the pH of the cosmetic compositions is from about 3 to less than 7, about 3.5 to less than 7, about 4 to less than 7, about 3 to about 6.5, about 3.5 to about 6.5, about 4 to about 6.5, about 3 to about 6, about 3.5 to about 6, about 4 to about 6, about 3 to about 5.5, or about 3.5 to about 5.5.

Viscosity

The viscosity of the cosmetic composition will vary. Nonetheless, in certain embodiments, the viscosity of the cosmetic composition is from 10,000 to about 100,000 cPa·s at 25° C., and shear rate of 1 s$^{-1}$. In further embodiments, the viscosity is from about 10,000 to about 80,000 cPa·s, about 10,000 to about 60,000 cPa·s, about 10,000 to about 50,000 cPa·s, about 20,000 to about 100,000 cPa·s, about 20,000 to about 80,000 cPa·s, about 20,000 to about 60,000 cPa·s, about 25,000 to about 100,000 cPa·s, about 25,000 to about 80,000 cPa·s, or about 25,000 to about 60,000 cPa·s at 25° C., and shear rate of 1 s$^{-1}$.

Methods

The instant disclosure also relates to methods of treating skin. The methods include applying the cosmetic compositions to the skin. The cosmetic compositions are typically applied directly to the skin using the hands or a cloth. The skin may be optionally washed or rinsed prior to application. The method for treating the skin can be carried out once daily or may be carried out multiple times per day. For example, the method for treating skin may be carried out once daily, twice daily, weekly, bi-weekly; and may be carried out for an extended period of time, for example, for 1, 2, 3, 4, 5, or 6 months. The methods dissolve dead skin cells, improve the appearance of fine lines and discoloration, remove excess oil from the skin, improve skin texture and tone, and/or hydrates the skin.

Embodiments In preferred embodiments, the cosmetic composition comprises or consists of:
(a) poly C10-30 alkyl acrylate, preferably about 0.5 to about 3 wt. %, more preferably about 0.5 to about 2 wt. %, even more preferably about 0.5 to about 1.5 wt. % of poly C10-30 alkyl acrylate;
(b) at least 5 wt. % of one or more lactone polyols, preferably at least 5 to about 15 wt. %, more preferably about 5 to about 10 wt. % of one or more lactone polyols, preferably gluconolactone and/or 3-O-ethyl ascorbic acid;
   wherein an amount of the one or more lactone polyols of (b) is in an amount at least 10-fold higher than the poly C10-30 alkyl acrylate of (a), preferably at least 10-fold to about 25-fold higher, more preferably at least 10-fold to about 20-fold higher;
(c) one or more nonionic emulsifiers, preferably about 0.1 to about 5 wt. %, more preferably about 0.5 to about 4 wt. %, even more preferably about 1 to about 3 wt. % of one or more nonionic emulsifiers;
(d) one or more fatty compounds, preferably about 1 to about 25 wt. %, more preferably about 2 to about 20 wt. %, even more preferably about 5 to about 15 wt. % of one or more fatty compounds, for example, one or more fatty compounds selected from:
  (d)(1) one or more fatty alcohols, preferably about 0.1 to about 5 wt. %, more preferably about 0.2 to about 4 wt. %, more preferably about 0.5 to about 3 wt. % of one or more fatty alcohols;
  (d)(2) one or more fatty carbonate esters, preferably about 0.1 to about 15 wt. %, more preferably about 1 to about 12 wt. %, even more preferably about 2 to about 8 wt. % of one or more fatty carbonate esters; and/or
  (d)(3) one or more volatile hydrocarbons, preferably about 0.1 to about 12 wt. %, more preferably about 0.5 to about 10 wt. %, even more preferably about 1 to about 8 wt. % of one or more volatile hydrocarbons;
(e) water, preferably about 50 to about 85 wt. % of water, more preferably about 55 to about 80 wt. %, even more preferably about 55 to about 75 wt. % of water;
(f) one or more thickening agents, preferably about 0.1 to about 5 wt. %, more preferably about 0.5 to about 4 wt. %, more preferably about 0.5 to about 3 wt. % of one or more thickening agents, for example, one or more thickening agents selected from:
  (f)(1) one or more taurate polymers or copolymers, preferably about 0.01 to about 5 wt. %, more preferably about 0.1 to about 4 wt. %, more preferably about 0.1 to about 3 wt. % of one or more taurate polymers or copolymers; and
  (f)(1) one or more crosslinked polyacrylate polymers, preferably about 0.01 to about 5 wt. %, more preferably about 0.1 to about 4 wt. %, more preferably about 0.1 to about 3 wt. %;
(g) one or more alpha hydroxy acids, beta hydroxy acids, salts thereof, or a combination thereof, preferably 0.1 to about 10 wt. %, more preferably about 1 to about 10 wt. %, even more preferably about 2 to about 8 wt. % of one or more alpha hydroxy acids, beta hydroxy acids, salts thereof, or a combination thereof;
(h) one or more water-soluble organic solvents, preferably from about 0.1 to about 20 wt. %, more preferably about 0.5 to about 18 wt. %, even more preferably about 1 to about 15 wt. % of one or more water-soluble organic solvents;
(i) optionally, one or more miscellaneous ingredients, preferably about 0.01 to about 10 wt. %, more preferably about 0.1 to about 8 wt. %, more preferably about 1 to about 6 wt. % of one or more miscellaneous ingredients;
   wherein all weight percentages are based on a total weight of the composition.

In another embodiment, the cosmetic composition comprises or consists of:
(a) about 0.5 to about 3 wt. %, preferably about 0.5 to about 2 wt. %, more preferably about 0.5 to about 1.5 wt. % of poly C10-30 alkyl acrylate;
(b) at least 5 wt. % of one or more lactone polyols, preferably at least 5 to about 15 wt. %, more preferably about 5 to about 10 wt. % of one or more lactone polyols, preferably gluconolactone and/or 3-O-ethyl ascorbic acid;
   wherein the one or more lactone polyols of (b) are in an amount at least 10-fold higher than an amount of the poly C10-30 alkyl acrylate of (a), preferably at least 10-fold to about 25-fold higher, more preferably at least 10-fold to about 20-fold higher;
(c) about 0.1 to about 5 wt. %, preferably about 0.5 to about 4 wt. %, more preferably about 1 to about 3 wt. % of one or more nonionic emulsifiers, in particular, one or more nonionic emulsifiers selected from fatty acid esters of sucrose, fatty acid esters of polyethylene glycol, glyceryl esters of fatty acids, alkanolamides, ethoxylate amides, alkylated alcohols, alkylpolypolyglucosides, sorbitan esters, polyol esters and ethoxylates, ethylene glycol ethers of fatty alcohols, fatty alcohol ethoxylates, and a mixture thereof;
(d) about 1 to about 25 wt. %, preferably about 2 to about 20 wt. %, more preferably about 5 to about 15 wt. % of one or more fatty compounds, for example, one or more fatty compounds selected from:
  (d)(1) about 0.1 to about 5 wt. %, preferably about 0.2 to about 4 wt. %, more preferably about 0.5 to about 3 wt. % of one or more fatty alcohols, in particular, one or more fatty alcohols selected from cetyl alcohol, stearyl alcohol, behenyl alcohol and mixtures thereof, preferably cetyl alcohol, behenyl alcohol, cetearyl alcohol, and combination thereof;
  (d)(2) about 0.1 to about 15 wt. %, preferably about 1 to about 12 wt. %, more preferably about 2 to about 8 wt. % of one or more fatty carbonate esters, in particular one or more fatty carbonate esters of formula: $R_1O(C=O)OR_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably dicaprylyl carbonate; and/or
  (d)(3) about 0.1 to about 12 wt. %, preferably about 0.5 to about 10 wt. %, more preferably about 1 to about 8 wt. % of one or more volatile hydrocarbons, in particular, one or more volatile hydrocarbons selected from isoparaffin, isohexadecane, isododecane, isodecane, undecane, tridecane, dodecane, isohexyl, isodecyl, neopentanoate, C15-19 alkane, and a combination thereof;

(e) about 50 to about 85 wt. % of water, more preferably about 55 to about 80 wt. %, even more preferably about 55 to about 75 wt. % of water;

(f) about 0.1 to about 5 wt. %, preferably about 0.5 to about 4 wt. %, more preferably about 0.5 to about 3 wt. % of one or more thickening agents, for example, one or more thickening agents selected from:

(f)(1) one or more taurate polymers or copolymers, preferably about 0.01 to about 5 wt. %, more preferably about 0.1 to about 4 wt. %, more preferably about 0.1 to about 3 wt. % of one or more taurate polymers or copolymers, in particular, one or more taurate polymers or copolymers selected from acrylamide/sodium acryloyl dimethyl taurate copolymer, ammonium polyacryloyldimethyl taurate, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, and a mixture thereof, preferably selected from hydroxyethyl acrylate/sodium acryloyldimethyl taurate copolymer, ammonium acryloyldimethyl taurate/VP copolymer, ammonium polyacryloyldimethyl taurate, and a mixture thereof; and (f)(1) about 0.01 to about 5 wt. %, more preferably about 0.1 to about 4 wt. %, more preferably about 0.1 to about 3 wt. % of one or more crosslinked polyacrylate polymers (polyacrylate crosspolymers), preferably polyacrylate crosspolymer-6;

(g) about 0.1 to about 10 wt. %, preferably about 1 to about 10 wt. %, more preferably about 2 to about 8 wt. % of one or more alpha hydroxy acids, beta hydroxy acids, salts thereof, or a combination thereof, for example, (g)(1) about 0.1 to about 10 wt. %, preferably about 1 to about 8 wt. %, more preferably about 2 to about 6 wt. % of one or more alpha hydroxy acids selected from glycolic acid, lactic acid, phytic acid, citric acid, malic acid, tartaric acid, a salt thereof, and a combination thereof, preferably a combination of glycolic acid, lactic acid, and phytic acid;

(g)(2) about 0.01 to about 5 wt. %, preferably about 0.1 to about 4 wt. %, more preferably about 0.1 to about 2 wt. % of one or more beta hydroxy acids selected from salicylic acid, beta-hydroxybutanoic acid, tropic acid, trethocanic acid, and a combination thereof, preferably salicylic acid;

(h) about 0.1 to about 20 wt. %, preferably about 0.5 to about 18 wt. %, more preferably about 1 to about 15 wt. % of one or more water-soluble organic solvents selected from glycerin, $C_2$-$C_5$ mono-alcohols, polyols (polyhydric alcohols), glycols, and a mixture thereof, preferably glycerin and one or more glycols such as propylene glycol, butylene glycol, or a combination thereof;

(i) optionally, about 0.01 to about 10 wt. %, preferably about 0.1 to about 8 wt. %, more preferably about 1 to about 6 wt. % of one or more miscellaneous ingredients selected from preservatives, fragrances, pH adjusters, salts, buffers, antioxidants, flavonoids, vitamins, botanical extracts, UV filtering agents, proteins, protein hydrolysates and/or isolates, hydrotropes, pearlescent agents, fillers, colorants, mattifying agents, further skin active agents, depigmenting agents, anti-wrinkle agents, and a combination thereof;

wherein all weight percentages are based on a total weight of the composition.

In various embodiments, the cosmetic composition is free or essentially free from polyorganosiloxanes (silicones). In various embodiments, the cosmetic composition is free or essentially free from amino silicones, for example, amodimethicone.

The cosmetic compositions can be in a variety of forms. For example, in many instances, the compositions are in the form of a liquid, gel, lotion, crème, and/or spray. The compositions may be packaged in a variety of different containers. Nonlimiting examples of useful packaging include tubes, jars, caps, unit dose packages, bags, and bottles, including squeezable tubes and bottles.

EXAMPLES

As various changes could be made in the above-described methods without departing from the scope of the invention, it is intended that all matter contained in the above description and in the examples given below, shall be interpreted as illustrative and not in a limiting sense. The ingredient amounts in the compositions/formulas described below are expressed in % by weight, based on the total weight of the composition.

Example 1

| | | | A | B | C | D |
|---|---|---|---|---|---|---|
| (a) | Stabilizer | POLY C10-30 ALKYL ACRYLATE | 0.5 | | 0.6 | |
| (b) | Skin Active | GLUCONOLACTONE | 5 | 5 | | |
| | | 3-O-ETHYL ASCORBIC ACID | | | 10 | 10 |
| | | Weight Ratio of (a):(b) | 1:10 | NA | 1:17 | NA |
| (c) | Water-Soluble Solvent | CAPRYLYL GLYCOL | | | 0.3 | 0.3 |
| | | BUTYLENE GLYCOL | 4 | 4 | | |
| | | GLYCERIN | 3 | 3 | 3 | 3 |
| (d) | Nonionic Emulsifiers | GLYCERYL STEARATE, STEARETH-100, GLYCOL STEARATE, SORBITAN ISOSTEARATE, LAURETH-4, POLYSORBATE 60, AND/OR CETEARYL GLUCOSIDE | 1.3 | 1.3 | 1.4 | 1.4 |
| (e) | Fatty Compounds | CAPRYLIC/CAPRIC TRIGLYCERIDE, CETYL ALCOHOL, COCO-CAPRYLATE/CAPRATE SQUALANE, *ZINGIBER OFFICINALE* (GINGER) ROOT OIL, BEHENYL ALCOHOL, CETEARYL ALCOHOL, DICAPRYLYL CARBONATE, C15-19 ALKANE, ISOHEXADECANE, AND/OR HYDROGENATED JOJOBA OIL | 10.8 | 10.8 | 3.8 | 3.8 |
| (f) | Thickening Agents | HYDROXYETHYL ACRYLATE/SODIUM ACRYLOYLDIMETHYL TAURATE COPOLYMER | 0.4 | 0.4 | | |
| | | AMMONIUM POLYACRYLOYLDIMETHYL TAURATE | 1 | 1 | 0.8 | 0.8 |

-continued

|   |   |   | A | B | C | D |
|---|---|---|---|---|---|---|
|   |   | HYDROXYETHYLCELLULOSE |   |   | 0.2 | 0.2 |
| (h) | Alpha HA/Salt | GLYCOLIC ACID, LACTIC ACID, PHYTIC ACID, CITRIC ACID, AND/OR SODIUM CITRATE | 5.8 | 5.8 | 1.5 | 1.5 |
| (i) | Beta HA/Salt | SALICYLIC ACID | 0.2 | 0.2 |   |   |
| (j) | Vitamin | ASCORBYL TETRAISOPALMITATE |   |   | 5 | 5 |
|   | Active | CAFFEINE |   |   | 0.2 | 0.2 |
|   | Active | PANAX GINSENG ROOT EXTRACT |   |   | 1 | 1 |
|   |   | Additional Miscellaneous Ingredients such as preservatives, fragrances, pH adjusters, botanical extracts, vitamins and derivatives thereof, chelants, pigments/pearlescent agents, humectants/emollients, etc.[1] | ≤10 | ≤10 | ≤10 | ≤10 |
| (g) |   | WATER | qs | qs | qs | qs |
|   |   | pH | 4 | 4 | 4.4 | 4.4 |
|   |   | Tacky | 1.8 | 3 | 3.3 | 5 |
|   |   | Tacky (stdev) | 0.3 | 0.5 | 0.9 | 0 |

[1]For example, chlorphenesin and/or phenoxyethanol (preservatives); tocopherol (vitamin/preservative); sodium hydroxide (pH adjuster); ilex paraguariensis leaf extract, passiflora edulis fruit extract, and/or hylocereus undatus fruit extract (botanical extracts); trisodium ethylenediamine disuccinate (chelant); and/or synthetic fluorphlogopite, titanium dioxide, and/or tin oxide (pigments/pearlescent agents), lauryl lysine and/or C12-15 alkyl benzoate (humectants/emollients), etc.

Example 2

Tackiness

The compositions presented in Example 1 were tested on a silicone substrate and tested for tackiness. About 0.2 grams of each composition was applied to the silicone substrate (Skin FX Plate 115) that was pre-heated to 32° C. The applied composition was then spread over one-fourth the total surface area of the plate at a rate of one circling round per second for 15 seconds. The spread product was allowed to sit for 15 seconds and then spread an additional 15 circling rounds per second over the same area. The compositions were then allowed to sit for 2 minutes and the tackiness of the dried layers was assessed by a panel of 3 specialists. The specialist firmly pressed the index finger against the dried layer and withdrew the finger to assess the tackiness (stickiness) of the layer. The specialists ranked the tackiness on a scale from 1 to 5, where 1 represents little or no tack and 5 represents maximum tackiness. The results are presented in the table below.

| n = 3 | A | B | C | D |
|---|---|---|---|---|
| Average Tackiness | 1.8 | 3 | 3.3 | 5 |
| Standard Deviation | 0.3 | 0.5 | 0.9 | 0 |

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

Definitions

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

The term "a mixture thereof" (or "combination thereof") is interchangeable with the term "mixtures thereof" (or "combinations thereof"). Throughout the disclosure, if the term "a mixture thereof" is used, following a list of elements as shown in the following example where letters A-F represent the elements: "one or more elements selected from A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting. Appropriate counterions for the components described herein are known in the art.

The expression "one or more" means "at least one" and thus includes individual components as well as mixtures/combinations.

The term "plurality" means "more than one" or "two or more."

An "alkyl radical" is a linear or branched saturated hydrocarbon-based group, particularly C1-C8, more particularly C1-C6, preferably C1-C4 such as methyl, ethyl, isopropyl and tert-butyl.

An "alkoxy radical" is a alkyl-oxy wherein alkyl is as described herein before.

An "alkenyl radical" is a linear or branched unsaturated hydrocarbon-based group, particularly C2-C8, more particularly C2-C6, preferably C2-C4 such as ethylenyl, propylenyl.

An "alkylene radical" is a linear or branched divalent saturated C1-C8, in particular C1-C6, preferably C1-C4 hydrocarbon-based group such as methylene, ethylene or propylene.

Some of the various categories of components identified for the cosmetic compositions may overlap. In such cases where overlap may exist and the composition/product includes two overlapping components (or more than two overlapping components), an overlapping component does not represent more than one component. As an example, tocopherol may be considered both a "vitamin" and a "preservative." If a particular composition/product includes both a vitamin and a preservative, tocopherol can serve as only a vitamin or only a preservative (tocopherol does not simultaneously serve as both the vitamin and the preservative, even though it functionally provides more than one effect).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions may be modified with the term "about," whether or not expressly stated.

Additionally, all numbers are intended to represent exact values as additional embodiments, whether or not modified by the term "about." For example, "an amount of about 1%" can be modified to refer to exactly 1%. As a further example, "an amount of 1%" can be modified to refer to "about 1%." Unless otherwise indicated, the term "about" is understood to encompass a range of +/−5% from the stated number. However, in some embodiments, the term may be defined to encompass narrower ranges, for example, +/−1%, 2%, 3%, or 4% from the stated number.

Various components may be included as salts even if not explicitly stated. In other words, whenever a compound has the ability to be in the form of a salt, it is intended that salts are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts. However, additional cations such as ammonium ions, or alkanolammonium ions such as monoethanolammonium or triethanolammonium ions, may also form salts.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the composition (provided that an amount of less than 2% by weight does not materially affect the basic and novel characteristics of the claimed invention). Similarly, a composition "substantially free" or "essentially free" of a stated material may include less than 1.5 wt. %, less than 1 wt. %, less than 0.5 wt. %, less than 0.1 wt. %, less than 0.05 wt. %, or less than 0.01 wt. %, or none of the specified material. The term "substantially free" or "essentially free" as used herein may also mean that the specific material is not added to the composition but may still be present in a raw material that is included in the composition.

Furthermore, all components that are positively set forth in the instant disclosure may be negatively excluded from the claims, e.g., a claimed composition may be "free," "essentially free" (or "substantially free") of one or more components that are positively set forth in the instant disclosure. As an example, silicones can optionally be included in the cosmetic compositions but in some instances the compositions may be free or essentially free from silicones. Silicones are synthetic polymers made up of repeating units of siloxane, elemental silicon and oxygen, combined with other elements, most often carbon and hydrogen. Thus, silicones are also called polysiloxanes. In some instances, cosmetic compositions of the instant case can be free or essentially free from dimethicones, amomdimethicones, dimethiconols, cyclosiloxanes, siloxanes, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising:
   (a) about 0.3 to about 3 wt. % of poly C10-30 alkyl acrylate;
   (b) at least 5 wt. % of one or more lactone polyols, wherein (a) and (b) are in a weight ratio of 10:1 to 25:1 (a):(b));
   (c) about 0.5 to about 6 wt. % of one or more nonionic emulsifiers;
   (d) one or more fatty compounds;
   (e) about 50 to 80 wt. % of water; and
   (f) about 0.1 to about 8 wt. % of one or more thickening agents;
   wherein the composition is an oil-in-water emulsion, and
   all weight percentages are based on a total weight of the composition.

2. The composition of claim 1, wherein at least one of the one or more thickening agents is a taurate polymer or copolymer.

3. The composition of claim 2, wherein the taurate polymer or copolymer is selected from acrylamide/sodium acryloyl dimethyl taurate copolymer, ammonium polyacryloyldimethyl taurate, hydroxyethyl acrylate/sodium acryloyl dimethyl taurate copolymer, ammonium acryloyldimethyl taurate/VP copolymer, sodium acrylate/sodium acryloyl dimethyl taurate copolymer, hydroxyethyl acrylate/sodium acryloyldimethyl taurate copolymer, or mixtures thereof.

4. The composition of claim 1, further comprising:
   (g) one or more alpha hydroxy acids, beta hydroxy acids, salts thereof, or mixtures thereof.

5. The composition of claim 4 comprising one or more alpha hydroxy acids selected from glycolic acid, lactic acid, phytic acid, citric acid, malic acid, tartaric acid, a salt thereof, or mixtures thereof.

6. The composition of claim 4 comprising one or more beta hydroxy acids selected from salicylic acid, beta-hydroxybutanoic acid, tropic acid, trethocanic acid, or mixtures thereof.

7. The composition of claim 4 comprising at least 1 wt. % of the one or more alpha hydroxy acids, beta hydroxy acids, salts thereof, or mixtures thereof.

8. The cosmetic composition of claim 1, wherein at least one of the one or more fatty compounds of (d) is a fatty alcohol.

9. The cosmetic composition of claim 1, wherein the fatty alcohol is selected from cetyl alcohol, stearyl alcohol, behenyl alcohol, or mixtures thereof.

10. The cosmetic composition of claim 8 comprising about 0.1 to about 5 wt. % of the fatty alcohol.

11. The cosmetic composition of claim 10, wherein the composition comprises one or more fatty compounds in addition to the at least one fatty alcohol selected from mineral oil, alkanes, fatty acids, fatty alcohol derivatives, fatty acid derivatives, esters of fatty alcohols, hydroxy-substituted fatty acids, waxes, fatty esters, fatty carbonate esters, triglyceride compounds, lanolin, silicone oils, or mixtures thereof.

12. The cosmetic composition of claim 1 comprising about 1 to about 20 wt. % of the one or more fatty compounds.

13. The composition of claim 1 wherein at least one of the one or more fatty compounds of (d) is a volatile hydrocarbon.

14. The composition of claim 13, wherein the volatile hydrocarbon is selected from isoparaffin, isohexadecane, isododecane, isodecane, undecane, tridecane, dodecane, isohexyl, isodecyl, neopentanoate, C15-19 alkane, or mixtures thereof.

15. The composition of claim 1, further comprising:
(g) one or more water-soluble organic solvents selected from glycerin, $C_2$-$C_5$ mono-alcohols, polyols, glycols, or mixtures thereof.

16. The composition of claim 1 having a pH of about 3.5 to about 6.5.

17. A cosmetic composition comprising:
(a) about 0.5 to about 1.5 wt. % of poly C10-30 alkyl acrylate;
(b) at least 5 to about 15 wt. % of gluconolactone, 3-O-ethyl ascorbic acid, or a combination thereof; wherein (b) is in an amount at least 10-fold higher than (a);
(c) about 0.1 to about 5 wt. % of one or more nonionic emulsifiers;
(d) about 5 to about 25 wt. % of a plurality of fatty compounds, wherein the plurality of fatty compounds comprises:
(d)(1) about 0.1 to about 5 wt. % of one or more fatty alcohols;
(d)(2) about 1 to about 10 wt. % of one or more fatty compounds in addition to the one or more fatty alcohols;
(e) about 50 to about 85 wt. % of water;
(f) about 0.1 to about 5 wt. % of one or more thickening agents, wherein at least one of the one or more thickening agents is selected from taurate polymers and copolymers;
(g) about 5 to about 10 wt. % of one or more alpha hydroxy acids, beta hydroxy acids, salts thereof, or a combination thereof;
(h) about 5 to about 20 wt. % of one or more water-soluble organic solvents selected from glycerin, $C_2$-$C_5$ mono-alcohols, polyols, glycols, or mixtures thereof;
wherein the composition is an oil-in-water emulsion, and all weight percentages are based on a total weight of the composition.

18. A method for treating skin comprising apply the composition of claim 1 to the skin.

19. The composition of claim 1, wherein the composition forms a dried layer that is less tacky than a comparative composition lacking poly C10-30 alkyl acrylate but is otherwise identical to the composition.

20. The composition of claim 17, wherein the composition forms a dried layer that is less tacky than a comparative composition lacking poly C10-30 alkyl acrylate but is otherwise identical to the composition.

* * * * *